US008715972B2

(12) United States Patent
Kondo et al.

(10) Patent No.: US 8,715,972 B2
(45) Date of Patent: May 6, 2014

(54) HOMOLACTIC FERMENTATION FROM PENTOSE

(75) Inventors: Akihiko Kondo, Kobe (JP); Kenji Okano, Kobe (JP); Hideo Noda, Amagasaki (JP)

(73) Assignees: Bio-energy Corporation (JP); Kansai Chemical Engineering Co., Ltd. (JP)

( * ) Notice: Subject to any disclaimer, the term of this patent is extended or adjusted under 35 U.S.C. 154(b) by 99 days.

(21) Appl. No.: 13/202,218

(22) PCT Filed: Feb. 15, 2010

(86) PCT No.: PCT/JP2010/052216
§ 371 (c)(1),
(2), (4) Date: Nov. 7, 2011

(87) PCT Pub. No.: WO2010/095600
PCT Pub. Date: Aug. 26, 2010

(65) Prior Publication Data
US 2012/0058528 A1 Mar. 8, 2012

(30) Foreign Application Priority Data
Feb. 18, 2009 (JP) ................................. 2009-035285

(51) Int. Cl.
*C12P 7/56* (2006.01)
*C12N 1/20* (2006.01)
*C12N 15/00* (2006.01)
*C12N 15/87* (2006.01)
*C12N 15/74* (2006.01)

(52) U.S. Cl.
USPC ........ 435/139; 435/252.3; 435/440; 435/463; 435/471

(58) Field of Classification Search
USPC .......... 435/162, 41, 471, 139, 252.3, 440, 463
See application file for complete search history.

(56) References Cited

U.S. PATENT DOCUMENTS

| | | | | |
|---|---|---|---|---|
| 5,798,237 | A * | 8/1998 | Picataggio et al. ........... | 435/139 |
| 7,083,955 | B2 * | 8/2006 | Otto ............................. | 435/139 |
| 2007/0037265 | A1 * | 2/2007 | Zhou et al. .................... | 435/139 |

OTHER PUBLICATIONS

Barre P., Identification of Thermobacteria and Homofermentative, Thermophilic, Pentose-utilizing *Lactobacilli* from High Temperature Fermenting Grape Musts, 1978, Journal of Applied Bacteriology, vol. 44, pp. 125-129.*
Walfridsson et al., Xylose-metabolizing *Saccharomyces cerevisiae* strains overexpressing the TKL1 and TAL1 genes encoding the pentose phosphate pathway enzymes transketolase and transaldolase, 1995, Applied and Environmental Microbiology, vol. 61(12), pp. 4184-4189.*
Posthuma et al., Expression of the Xylulose 5-Phosphate Phosphoketolase Gene, xpkA, from *Lactobacillus pentosus* MD363 is Induced by Sugars That are Fermented via the Phosphoketolase Pathway and is Repressed by Glucose Mediated by CcpA and the Mannose Phosphoenolpyruvate . . . PTS , 2002, Applied and Environmental Microbiology, vol. 68, pp. 831-837.*
Kovar et al., Stoichiometry of glucose and xylose fermentation in *Butyrivibrio fibrisolvens* 787, 1996, Ukrainskiĭ biokhimicheskiĭ zhurnal (Ukrainian biochemistry), vol. 68(5), pp. 85-89.*
Tanaka et al., Two different pathways for D-xylose metabolism and the effect of xylose concentration on the yield coefficient of L-lactate in mixed-acid fermentation by the lactic acid bacterium *Lactococcus lactis* IO-1, 2002, Applied Microbiology and Biotechnology, vol. 60, pp. 160-167.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kleerebezem et al., Complete geneome sequence of *Lactobacillus plantarum* WCFS1. PNAS., 2003, vol. 100 (4): 1990-1995.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Yevenes et al., Cloning, expression, purification, cofactor requirements, and steady state kinetics of phosphoketolase-2 from *Lactobacillus plantarum*. Bioorganic Chem., 2008, vol. 36: 121-127.*
Bustos, Guadalupe et al., "Influence of the Metabolism Pathway on Lactic Acid Production from Hemicellulosic Trimming Vine Shoots Hydrolyzates Using *Lactobacillus pentosus*", Biotechnol. Prog. 2005, vol. 21, No. 3, pp. 793-798, American Chemical Society and American Institute of Chemical Engineers.
Chaillou, Stephane et al., "Molecular Cloning and Functional Expression in *Lactobacillus plantarum* 80 of xylT, Encoding the D-Xylose—H+ Symporter of *Lactobacillus brevis*", Applied and Environmental Microbiology, Dec. 1998, vol. 64, No. 12, pp. 4720-4728, American Society for Microbiology.
Helanto, M. et al., "Metabolic Engineering of *Lactobacillus plantarum* for Production of L-Ribulose", Applied and Environmental Microbiology, Nov. 2007, vol. 73, No. 21, pp. 7083-7091, American Society for Microbiology.

(Continued)

*Primary Examiner* — Ganapathirama Raghu
(74) *Attorney, Agent, or Firm* — The Webb Law Firm (57) ABSTRACT

Provided is a lactic acid bacterium capable of homolactic fermentation using a pentose as a substrate, the lactic acid bacterium utilizing a pentose, and in which a phosphoketolase pathway is blocked and a pentose phosphate pathway is activated. Also provided is a method for producing lactic acid from a pentose using the lactic acid bacterium and a method for preparing the lactic acid bacterium.

6 Claims, 5 Drawing Sheets

(56) References Cited

OTHER PUBLICATIONS

Ohara, Hitomi et al., "Xylooligosaccharide Fermentation with *Leuconostoc lactis*", Journal of Bioscience and Bioengineering, 2006, vol. 101, No. 5, pp. 415-420, The Society for Biotechnology, Japan.

Tanaka, K. et al., Two different pathways for D-xylose metabolism and the effect of xylose concentration on the yield coefficient of L-lactate in mixed-acid fermentation by the lactic acid bacterium *Lactococcus lactis* IO-1, Appl. Microbiol. Biotechnol., 2002, vol. 60, pp. 160-167, Springer-Verlag.

Posthuma, Clara C. et al., "Expression of the Xylulose 5-Phosphate Phosphoketolase Gene, xpkA, from *Lactobacillus pentosus* MD363 is Induced by Sugars That are Fermented via the Phosphoketolase Pathway and is Repressed by Glucose Mediated by CcpA and the Mannose Phosphoenolpyruvate Phosphotransferase System", Feb. 2002, vol. 68, No. 2, pp. 831-837, American Society for Microbiology.

Okano, Kenji et al., "Efficient Production of Optically Pure D-Lactic Acid from Raw Corn Starch by Using a Genetically Modified L-Lactate Dehydrogenase Gene-Deficient and alpha-Amylase-Secreting *Lactobacillus plantarum* Strain", Applied and Environmental Microbiology, Jan. 2009, vol 75, No. 2, pp. 462-467, American Society for Microbiology.

Maguin, Emmanuelle et al., "Efficient Insertional Mutagenesis in *Lactococci* and Other Gram-Positive Bacteria", Journal of Bacteriology, Feb. 1996, vol. 178, No. 3, pp. 931-935, American Society for Microbiology.

Mora, D. et al., "Characterization of urease genes cluster of *Streptococcus thermophilus*", Journal of Applied Microbiology, 2004, 96, pp. 209-219, The Society for Applied Microbiology.

Katahira, Satoshi et al., "Ethanol fermentation from lignocellulosic hydrolysate by a recombinant xylose- and cellooligosaccharide-assimilating yeast strain", Appl. Microbiol. Biotechnol. 2006, vol. 72, pp. 1136-1143, Springer-Verlag.

Narita, Junya et al., "Display of alpha-Amylase on the Surface of *Lactobacillus casei* Cells by Use of the PgsA Anchor Protein, and Production of Lactic Acid from Starch", Applied and Environmental Microbiology, Jan. 2006, vol. 72, No. 1, pp. 269-275, American Society for Microbiology.

Okano, Kenji et al., "Improvement in lactic acid production from starch using alpha-amylase-secreting *Lactococcus lactis* cells adapted to maltose or starch", Appl. Microbiol. Biotechnol., 2007, vol. 75, pp. 1007-1013, Springer.

Lokman, B. Christien et al., Organization and characterization of three genes involved in D-xylose catabolism in *Lactobacillus pentosus*, Mol. Gen. Genet., 1991, vol. 230, pp. 161-169, Springer-Verlag.

Kovar, L. et al., Stoichiometry of Glucose and Xylos Fermentation in Butyrivibrio Fibrisolvens 787, Ukrainskii Biokhimicheskii Zhurnal, 1996, vol. 68, pp. 85-89.

Posthuma, Clara C. et al., "Expression of the Xylulose 5-Phosphate Phosphoketolase Gene, xpkA, from *Lactobacillus pentosus* MD363 is Induced by Sugars That are Fermented via the Phosphoketolase Pathway and is Repressed by Glucose Mediated by CcpA and the Mannose Phosphoenolpyruvate Phosphotransferase System", Applied and Environmental Microbiology, Feb. 2002, vol. 68, No. 2, pp. 831-837, American Society for Microbiology.

Okano, Kenji et al., "Homo-D-Lactic Acid Fermentation from Arabinose by Redirection of the Phosphoketolase Pathway to the Pentose Phosphate Pathway in L-Lactate Dehydrogenase Gene-Deficient *Lactobacillus plantarum*", Applied and Environmental Microbiology, Aug. 2009, vol. 75, No. 15, pp. 5175-5178, American Society for Microbiology.

\* cited by examiner

HOMOLACTIC FERMENTATION FROM PENTOSE

TECHNICAL FIELD

The present invention relates to lactic fermentation by a lactic acid bacterium, in particular, homolactic fermentation from a pentose.

BACKGROUND ART

Lignocellulose is an inexpensive and abundant inedible biomass source and consists of three main components: cellulose, hemicellulose, and lignin. Lignin is used as a fuel for direct burning. It is desired that lactic acid is produced from the two other components, cellulose and hemicellulose. Cellulose consists of glucose, which is available for lactic acid bacteria, while hemicellulose consists primarily of pentoses, such as xylose and arabinose, which are unavailable for most lactic acid bacteria. Accordingly, development of a technique for lactic acid production from a pentose is demanded.

To date, some lactic acid bacteria, such as *Lactobacillus pentosus* (Non-Patent Document 1), *Lactobacillus brevis* (Non-Patent Document 2), *Lactobacillus plantarum* (Non-Patent Document 3), and *Leuconostoc lactis* (Non-Patent Document 4), have been reported to utilize either or both of xylose and arabinose. Such lactic acid bacteria produce equimolar amounts of lactic acid and acetic acid simultaneously, which is called "heterolactic fermentation", without known exception.

Figure 1:
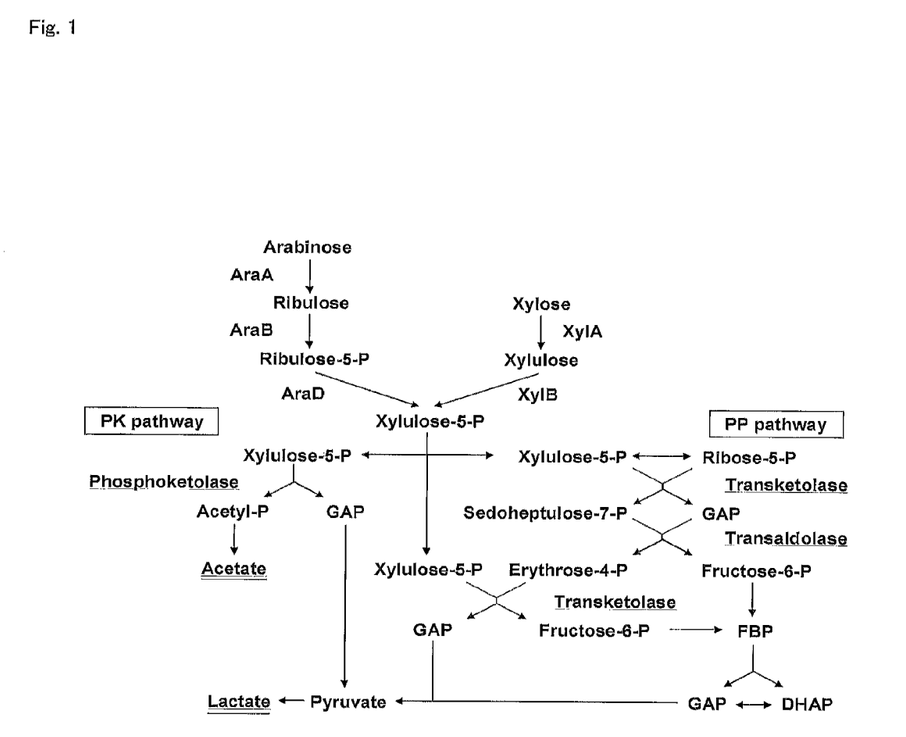
FIG. 1 shows a scheme of the pathways for xylose and arabinose utilization.

FIG. 1 shows a scheme of pathways for xylose and arabinose utilization. As shown in FIG. 1, xylose and arabinose are converted to xylulose 5-phosphate (X5P) by a series of intracellular metabolic enzymes in a lactic acid bacterium. During heterolactic fermentation, X5P is then cleaved by an action of a phosphoketolase into equimolar amounts of glyceraldehyde 3-phosphate (GAP) and acetyl phosphate (Acetyl-P), which are eventually converted to lactate and acetate, respectively (Non-Patent Document 5). This pathway is called a phosphoketolase (PK) pathway. Meanwhile, also known as a pathway for lactic fermentation by pentose utilization is a pentose phosphate (PP) pathway, in which GAP and fructose 6-phosphate (F6P) are yielded from X5P, and lactate alone is eventually produced. This is called "homolactic fermentation."

*Lactococcus lactis* IO-1 is known to have the PP pathway in addition to the PK pathway and produce lactic acid at more than the equimolar amount, however, complete homolactic fermentation has not been achieved (Non-Patent Document 5). No lactic acid bacterium that is capable of homolactic fermentation from a pentose has been reported so far.

It has been reported that *Lactobacillus pentosus* loses its ability to grow on pentoses due to a defect in a gene for phosphoketolase, an enzyme that acts in the PK pathway (Non-Patent Document 6). However, no report has described introduction of the PP pathway.

PRIOR ART DOCUMENTS

Non-Patent Documents

Non-Patent Document 1: Bustos, G. et al, 2005, Biotechnol. Prog., 21: 793-798
Non-Patent Document 2: Chaillou, S. et al, 1998, Appl. Environ. Microbiol., 64: 4720-4728
Non-Patent Document 3: Helanto, M. et al., 2007, Appl. Environ. Microbiol., 73: 7083-7091
Non-Patent Document 4: Ohara, H. et al., 2006, J. Biosci. Bioeng., 101: 415-420
Non-Patent Document 5: Tanaka, K. et al, 2002, Appl. Microbiol. Biotechnol., 60: 160-167
Non-Patent Document 6: Posthuma, C. C. et al, 2002, Appl. Environ. Microbiol., 68: 831-837
Non-Patent Document 7: Okano, K. et al, 2009, Appl. Environ. Microbiol., 75: 462-467
Non-Patent Document 8: Maguin, E. et al, 1996, J. Bacteriol., 178: 931-935
Non-Patent Document 9: Mora, D. et al, 2004, J. Appl. Microbiol. 96: 209-219
Non-Patent Document 10: Katahira, S. et al, 2006, Appl. Microbiol. Biotechnol., 72: 1136-1143
Non-Patent Document 11: Narita, J. et al, 2006, Appl. Environ. Microbiol., 72: 269-275
Non-Patent Document 12: Okano, K. et al., 2007, Appl. Microbiol. Biotechnol., 75: 1007-1013
Non-Patent Document 13: Lokman, B. C. et al., 1991, Mol. Gen. Genet., 230: 161-169

SUMMARY OF INVENTION

Problems to be Solved by the Invention

An object of the present invention is to provide a lactic acid bacterium that is capable of homolactic fermentation from a pentose.

Means for Solving the Problems

The present invention provides a lactic acid bacterium capable of homolactic fermentation using a pentose as a substrate, the lactic acid bacterium utilizing a pentose, and in which a phosphoketolase pathway is blocked and a pentose phosphate pathway is activated.

The present invention also provides a method for producing lactic acid, comprising: allowing the lactic acid bacterium to act on a pentose.

The present invention further provides a method for preparing a lactic acid bacterium capable of homolactic fermentation using a pentose as a substrate, comprising:
providing a pentose-utilizing lactic acid bacterium; and
causing a defect in a gene encoding a phosphoketolase in the lactic acid bacterium to block a phosphoketolase pathway.

In an embodiment, the method further comprises: introducing at least one of a gene encoding a transketolase and a gene encoding a transaldolase into the lactic acid bacterium to activate a pentose phosphate pathway.

Effects of Invention

The present invention provides a lactic acid bacterium that is capable of homolactic fermentation from a pentose. Lactic acid can be produced effectively by such a lactic acid bacterium using a pentose as a substrate.

DETAILED DESCRIPTION OF THE INVENTION

According to the present invention, homolactic fermentation from a pentose can be achieved by blocking the PK pathway and activating the PP pathway in a pentose-utilizing lactic acid bacterium. Herein, the lactic acid bacterium of the present invention may also be referred to as a pentose-utilizing homolactic-fermenting lactic acid bacterium.

The term "pentose" can refer to any pentose (sugar composed of five carbons) used in the metabolism of a lactic acid bacterium, and preferred examples include arabinose and xylose.

According to the present invention, a pentose-utilizing lactic acid bacterium is used. A pentose-utilizing bacterium is capable of utilizing at least one of arabinose and xylose as a substrate to produce lactic acid by fermentation. Examples of bacteria that are capable of utilizing at least one of arabinose and xylose include lactic acid bacteria such as Lactobacillus pentosus, Lactobacillus brevis, Lactobacillus plantarum, and Leuconostoc lactis To provide a pentose-utilizing lactic acid bacterium, a bacterium that assimilates arabinose by nature may be imparted with a xylose-utilizing ability or vice versa. Alternatively, a bacterium that is capable of utilizing a hexose (sugar composed of six carbons), such as glucose, may be imparted with an arabinose-utilizing ability and/or a xylose-utilizing ability.

As shown in FIG. 1, xylose is converted by two enzymes, more specifically, to xylulose by a xylose isomerase (encoded by xylA) and then to xylulose 5-phosphate (X5P) by a xylulose kinase (encoded by xylB). Therefore, a xylose-utilizing ability is imparted by introducing at least one of, preferably both of xylA and xylB into a lactic acid bacterium to which the xylose-utilizing ability is imparted, depending on the gene possessed by the lactic acid bacterium.

As shown in FIG. 1, arabinose is converted to ribulose by an arabinose isomerase (encoded by araA), then to ribulose 5-phosphate by a ribulokinase (encoded by araB), and eventually to xylulose 5-phosphate (X5P) by a ribulose 5-phosphate 4-epimerase (encoded by araD). Therefore, an arabinose-utilizing ability is imparted by introducing at least one of preferably all of araA, araB, and araD into a lactic acid bacterium to which the arabinose-utilizing ability is imparted, depending on the gene possessed by the lactic acid bacterium.

According to the present invention, the PK pathway is blocked in a lactic acid bacterium. This blockage can suppress the acetic acid production resulting from pentose utilization. The action of a phosphoketolase is preferably inhibited by blocking the PK pathway. To this end, a defect in a gene encoding a phosphoketolase can be caused. Expression of the gene encoding a phosphoketolase can depend on the lactic acid bacterium used, culture conditions (for example, the type of sugar used as a substrate, pH, temperature, and oxygen status), and the like. It is preferable to cause a defect in the phosphoketolase gene in a lactic acid bacterium that can be usually expressed under applicable culture conditions. For example, Lactobacillus plantarum (in particular, strain NCIMB 8826) has two phosphoketolase-encoding genes: xpk1 and xpk2. When this strain utilizes arabinose, the PK pathway can be blocked if xpk1 is defective. When the strain utilizes xylose, the PK pathway can be successfully blocked by causing defects in both xpk1 and xpk2.

A defect in a gene may refer to a defect of at least a part of a gene on the chromosome so long as the encoded enzyme does not act normally. The defect in a gene can be achieved by, for example, gene disruption. Such gene disruption can be achieved by any method by which normal expression of a gene is interfered or inactivated by modification or deletion of the sequence of the target gene region, resulting in inhibition of normal gene expression and hence loss of a normal enzymatic action. Examples of methods for modifying the sequence of a gene region include substitution with another nucleotide sequence, deletion of a partial sequence, and division of the region by insertion of another nucleotide sequence. The defect in a gene can be caused using a method commonly used by those skilled in the art.

According to the present invention, the PP pathway is activated in a lactic acid bacterium. Activation of the PP pathway encompasses introduction of the PP pathway into a lactic acid bacterium as well as stimulation of the PP pathway. As shown in FIG. 1, a transketolase and a transaldolase can be involved in the PP pathway to produce GAP and F6P from X5P and eventually lactic acid alone. At least one of the gene encoding a transketolase and the gene encoding a transaldolase can be introduced, depending on the type of lactic acid bacterium used, to activate the PP pathway. An example of the gene encoding a transketolase may be the tkt gene (NCBI Gene ID: 1115285) from Lactococcus lactis (in particular, strain IL 1403). Known examples of the gene encoding a transaldolase include talA (NCBI Gene ID: 6060135) and talB (NCBI Gene ID: 6061856) from Escherichia coli strain K-12. A lactic acid bacterium in which the PP pathway is by nature activated (for example, a lactic acid bacterium possessing by nature a gene encoding at least one of the above-mentioned enzymes) can also be used according to the present invention. For example, since Lactococcus lactis strain IO-1 possesses transaldolase and transketolase activities (Non-Patent Document 5), genes for such enzymes from this strain can be used to activate the PP pathway in a lactic acid bacterium according to the present invention. Furthermore, a pentose-utilizing homolactic-fermenting lactic acid bacterium can also be prepared by blocking the PK pathway in a pentose-utilizing lactic acid bacterium possessing the PK pathway in addition to the PP pathway, such as Lactococcus lactis strain IO-1. For example, in Lactobacillus plantarum (in particular, strain NCIMB 8826), homolactic fermentation from a pentose has been successfully achieved by introducing the gene encoding a transketolase in addition to blocking the PK pathway.

Therefore, the present invention provides a pentose-utilizing lactic acid bacterium in which the PK pathway is blocked and the PP pathway is activated. The lactic acid bacterium can be modified for further improvement, such as inhibition of degradation of the produced lactic acid, or production of lactic acid with high optical purity. For example, Lactobacillus plantarum (in particular, strain NCIMB 8826) can produce D-lactic acid with high optical purity by inhibiting the action of L-lactate dehydrogenase (Non-Patent Document 7). Activation or inhibition of actions of enzymes for such modifications can similarly be made as described above.

According to the present invention, the term "homolactic fermentation" means fermentation in which lactic acid is primarily produced while production of acetic acid is inhibited. A pentose-utilizing homolactic-fermenting lactic acid bacterium can produce primarily lactic acid and virtually no acetic acid from a pentose. Lactic acid can be produced in an amount of, for example, 30 times or more, preferably 40 times or more, more preferably 50 times or more, further more preferably 75 times or more, further more preferably 95 times or more the amount of acetic acid.

The optical activity of the produced lactic acid can depend on the lactic acid bacterium used. For example, blocking the PK pathway and activating the PP pathway of the L-lactate dehydrogenase-disrupted strain of *Lactobacillus plantarum* (in particular, the L-lactate dehydrogenase-disrupted strain of NCIMB 8826 [Non-Patent Document 7]) that can produce D-lactic acid with high optical purity, as illustrated in the Examples, enables homo-fermentation of D-lactic acid with high optical purity.

According to the present invention, lactic acid can be produced (fermentation production) by allowing the above-mentioned pentose-utilizing homolactic-fermenting lactic acid bacterium to act on a pentose. The pentose-utilizing homolactic-fermenting lactic acid bacterium can be allowed to act on not only a single pentose (for example, either arabinose or xylose), but also a mixture of pentoses (for example, a combination of arabinose and xylose) as well as a mixture with a hexose (for example, glucose) so long as the lactic acid bacterium can utilize.

According to the present invention, production of lactic acid can be performed by a method commonly employed by those skilled in the art of lactic fermentation using a lactic acid bacterium. For example, lactic acid may be produced by simply cultivating the above-described pentose-utilizing homolactic-fermenting lactic acid bacterium together with a pentose. The conditions for cultivation, such as pH, temperature, and oxygen status, can be suitably selected.

According to the present invention, as described above, a lactic acid bacterium that is capable of homolactic fermentation using a pentose as a substrate can also be produced by blocking the PK pathway and, if necessary, activating the PP pathway in a pentose-utilizing lactic acid bacterium.

The acid produced by fermentation usually depends on the type of lactic acid bacterium, the conditions for cultivation (for example, the type of sugar used as a substrate, pH, temperature, and oxygen status), and the like. For example, some facultative hetero-fermentative bacteria primarily produce lactic acid using a hexose as a substrate while a substantial amount of acetic acid in addition to lactic acid using a pentose as a substrate. According to the present invention, however, homolactic fermentation from a pentose can be achieved, regardless of the type of pentose used as a substrate or the type of lactic acid bacterium. When the present invention is applied to a facultative hetero-fermentative bacterium, homolactic fermentation from a pentose and a hexose can also be achieved.

Hereafter, the present invention will now be illustrated with reference to the following Examples, but is not intended to be limited to these Examples.

EXAMPLES

Example 1

Homolactic Production from Arabinose (Materials and Methods)

As a host, the L-lactate dehydrogenase-disrupted strain of *Lactobacillus plantarum* NCIMB 8826 (Non-Patent Document 7), which produces D-lactic acid with high optical purity, was used. Hereinafter, this L-lactate dehydrogenase-disrupted strain of *Lactobacillus plantarum* NCIMB 8826 is also referred to simply as a "ΔldhL1 strain." This strain is by nature capable of utilizing arabinose. The *Lactobacillus plantarum* ΔldhL1 strain and a modified strain thereof were grown at 37° C. in MRS broth (Difco Laboratories, Detroit, Mich.) or MRS broth containing 25 μg/ml erythromycin. To the medium, 1.5% (w/v) agar was added to produce a solid medium. PCR was carried out using a KOD-Plus-polymerase (Toyobo Co., Ltd.). *Escherichia coli* VE 7108 (Non-Patent Document 9) was used for gene manipulation of pG+host9 (Non-Patent Document 8) and grown in Luria-Bertani (LB) medium containing 250 μg/ml of erythromycin and 10 μg/ml of kanamycin at 37° C.

(Construction of Plasmids)

A plasmid for disruption of a gene for phosphoketolase (the phosphoketolase 1 gene: *Lactobacillus plantarum* xpk1) was constructed as follows. The 520-bp upstream region from the start codon of xpk1 and the 1000-bp downstream region from the stop codon of xpk1 were amplified by PCR from the genome prepared from *Lactobacillus plantarum* NCIMB 8826 (obtained from NCIMB) by a conventional method using a pair of oligonucleotide primers xpk1-up_F (SEQ ID NO: 1) and xpk1-up_R (SEQ ID NO: 2) and a pair of xpk1-down_F (SEQ ID NO: 3) and xpk1-down_R (SEQ ID NO: 4). The resulting fragments were digested with SalI and then ligated. Using the ligated fragment (1520 bp) as a template, the same fragment was amplified by PCR with oligonucleotide primers xpk1-up_F (SEQ ID NO: 1) and xpk1-down_R (SEQ ID NO: 4). The amplified fragment was digested with XhoI and NotI and subsequently inserted between the XhoI and NotI sites of a plasmid pG+host9 (Non-Patent Document 8). The resulting plasmid was designated as pGh9-Δxpk1.

A plasmid for substitution of xpk1 with the gene for transketolase from *Lactococcus lactis* IL 1403 (tkt) was constructed as follows. The open reading frame of tkt was amplified by PCR from the genome prepared from *Lactococcus lactis* IL 1403 by a conventional method using oligonucleotide primers tkt_F (SEQ ID NO: 5) and tkt_R (SEQ ID NO: 6). The amplified fragment was digested with BglII and SalI and subsequently inserted between the BglII and SalI sites of the plasmid pGh9-Δxpk1. The resulting plasmid was designated as pGh9-xpk1::tkt.

Figure 2:
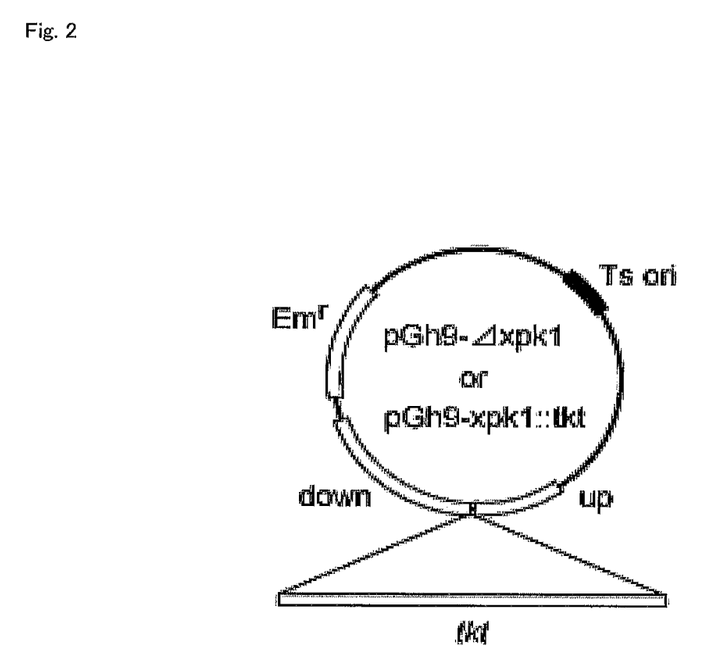
FIG. 2 is a schematic view of a plasmid (pGh9-Δxpk1) for disruption of a gene for phosphoketolase 1 (*Lactobacillus plantarum* xpk1) or a plasmid (pGh9-xpk1::tkt) for substitution with a gene for transketolase (tkt from *Lactococcus lactis* IL 1403)

FIG. 2 is a schematic view of a plasmid (pGh9-Δxpk1) for disruption of a gene for phosphoketolase 1 (*Lactobacillus plantarum* xpk1) or a plasmid (pGh9-xpk1::tkt) for substitution with a gene for transketolase (tkt from *Lactococcus lactis* IL 1403). In FIG. 2, Ts Ori represents temperature-sensitive replication origin; Emr represents erythromycin resistance gene; up represents the 520-bp upstream region from the start codon of the xpk1 gene; down represents the 1000-bp downstream region from the stop codon of the xpk1 gene; and tkt represents the open reading frame of tkt.

(Disruption and Substitution of xpk1 Gene of ΔldhL1 Strain)

Disruption and substitution of the xpk1 gene of the ΔldhL1 strain using pGh9-Δxpk1 and pGh9-xpk1::tkt were carried out by pG+host plasmid-based double-crossover homologous integration (Non-Patent Document 7). The resulting ΔldhL1 strain in which xpk1 was disrupted and the resulting ΔldhL1 strain in which xpk1 was substituted with tkt were designated as a ΔldhL1-Δxpk1 strain and a ΔldhL1-xpk1::tkt strain, respectively. Deletion and substitution of xpk1 were confirmed by performing PCR using a forward primer xpk1-up_seq (SEQ ID NO: 7) and a reverse primer xpk1-down_seq (SEQ ID NO: 8) (annealed to the region from by 282 through 300 upstream of xpk1 and the region from by 266 through 300 downstream of xpk1, respectively), comparing the bands on agarose gel electrophoresis, and DNA sequencing.

Effect of Disruption and Substitution of xpk1 Gene on Growth Using Arabinose as Carbon Source Cell growth with arabinose was confirmed by cultivation using arabinose as a sole carbon source. A modified MRS medium (MRS without glucose, beef extract, sodium acetate, and Tween 80) containing 2.0% (w/v) arabinose and lacking sugar was used for this assay, and the growth of *L. plantarum* cells was monitored by measuring the optical density ($OD_{600}$) at 600 nm after 12 hours of cultivation.

The ΔldhL1 strain was grown efficiently using arabinose as the sole carbon source ($OD_{600}$ of 1.48). In the case of control cultivation (without arabinose), growth decreased markedly ($OD_{600}$ of 0.59), while *Lactobacillus plantarum* cells grew only slightly without any sugar among medium components. On the other hand, the ΔldhL1-Δxpk1 strain showed poor growth with arabinose ($OD_{600}$ of 0.26) even compared with control cultivation ($OD_{600}$ of 0.45). This lack of growth was restored by introducing tkt into the xpk1 locus, and the resulting strain ΔldhL1-xpk1::tkt showed a higher $OD_{600}$ value, 1.73, than that for control cultivation ($OD_{600}$ of 0.56).

Lactic Fermentation from Arabinose Using ΔldhL1 and ΔldhL1-xpk1::tkt Strains

All fermentation experiments were performed in a 2-liter bioreactor (Able & Biott Co., Ltd., Tokyo, Japan) with a working volume of 700 ml. The fermenter contained a liquid-modified MRS medium that was heat-sterilized (121° C., 15 minutes). Then, a heat-sterilized arabinose solution was added to the fermenter (a final concentration, 50 g/l). Subsequently, 10 M $H_2SO_4$ was added to the medium in order to adjust the pH to 6.0, and 7 ml of inoculum (adjusted to an $OD_{600}$ of 10 with sterile distilled water) was added to the fermenter. Prior to this addition, the inoculum was grown in MRS and subcultured at regular intervals (12 h) to stabilize the growth rate. The temperature was maintained at 36° C., agitation speed was maintained at 100 rpm, and pH was kept at approximately 6.0 (±0.03) by automatic addition of 10 M $NH_3$ solution. After inoculation, the culture was regularly harvested and subjected to an analysis.

Growth of *Lactobacillus plantarum* cells was monitored by measuring $OD_{600}$. Arabinose concentration was measured by high performance liquid chromatography (HPLC), as described in Non-Patent Document 10, using a refractive index detector (model RID-10A; Shimadzu Corporation). The column used for the separation of L-arabinose was a Shim-pack SPR-Pb column (Shimadzu Corporation). HPLC was operated at 80° C. using water as a mobile phase at a flow rate of 0.6 ml/min. The concentrations of lactic acid and acetic acid were measured by HPLC as described in Non-Patent Document 11. The optical purity of lactic acid was measured using a BF-5 biosensor (Oji Scientific Instruments) as described in Non-Patent Document 7. The optical purity of lactic acid was defined as follows: Optical purity (%)=(D-lactic acid concentration−L-lactic acid concentration)/(D-lactic acid concentration+L-lactic acid concentration)×100.

Figure 3:
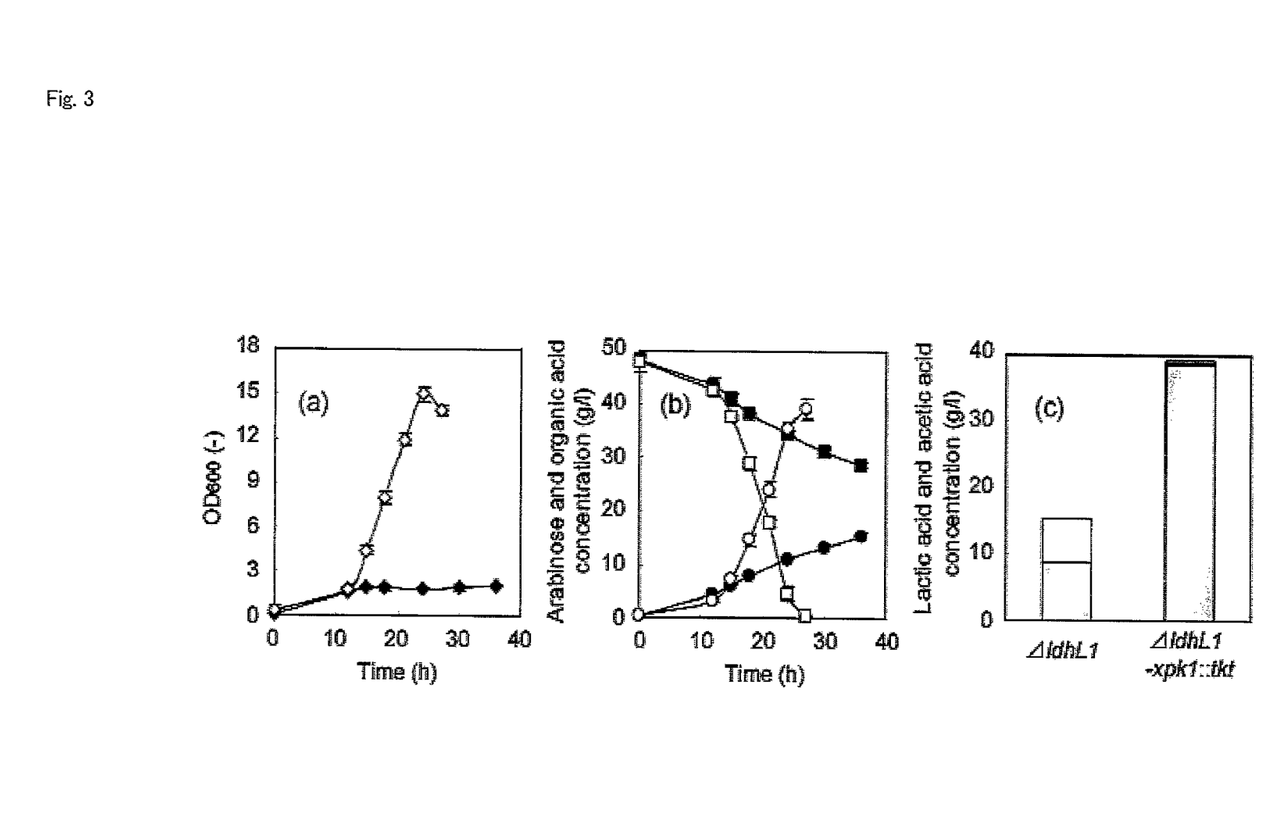
FIG. 3 shows graphs of (a) the $OD_{600}$ of culture, (b) the concentrations of arabinose and organic acid, and (c) the concentrations of lactic acid and acetic acid in fermentation experiments from arabinose using the ΔldhL1 and ΔldhL1-xpk1::tkt strains.

FIG. 3 shows graphs of (a) the $OD_{600}$ of culture, (b) the concentrations of arabinose and organic acid, and (c) the concentrations of lactic acid and acetic acid in fermentation experiments from arabinose using the ΔldhL1 and ΔldhL1-xpk1::tkt strains. In (a) of FIG. 3, the vertical axis represents the $OD_{600}$ value, and the horizontal axis represents the fermentation time (h). The results from the ΔldhL1 strain are indicated by closed diamonds, and the results from the ΔldhL1-xpk1::tkt strain are indicated by open diamonds. In (b) of FIG. 3, the vertical axis represents the concentrations of arabinose and organic acid (both in g/l), and the horizontal axis represents the fermentation time (h). The concentration of arabinose resulting from consumption by the ΔldhL1 strain is indicated by closed squares. The concentration of arabinose resulting from consumption by the ΔldhL1-xpk1::tkt strain is indicated by open squares. The concentration of organic acid (lactic acid and acetic acid combined) produced by the ΔldhL1 strain is indicated by closed circles. The concentration of organic acid produced by the ΔldhL1-xpk1::tkt strain is indicated by open circles. In (c) of FIG. 3, the vertical axis represents the concentrations of produced lactic acid and acetic acid (both in g/l). The concentration of lactic acid is shown below the divider in a bar, and the concentration of acetic acid is shown above the divider.

Surprisingly, the ΔldhL1-xpk1::tkt strain showed significantly higher growth, sugar consumption, and acid production rate when compared with the ΔldhL1 strain ((a) and (b) of FIG. 3). The $OD_{600}$ value for the ΔldhL1-xpk1::tkt strain increased with fermentation time and reached 14.9 after 24 hours of fermentation, while that of the ΔldhL1 strain was significantly lower, even after 36 hours of fermentation ((a) of FIG. 3). Differences in sugar consumption and acid production were also observed between the strains. The ΔldhL1-xpk1::tkt strain consumed all sugar within 27 hours of fermentation and produced 39.2 g/l of organic acid, while fermentation continued after 36 hours with the ΔldhL1 strain, with 19.6 g/l of arabinose being consumed and 15.2 g/l of organic acid being produced ((b) of FIG. 3).

As shown in (c) of FIG. 3, the ΔldhL1 strain produced both lactic acid and acetic acid (8.9 g/l and 6.4 g/l, respectively, approximately 1:1 in terms of mole), while the ΔldhL1-xpk1::tkt strain produced predominantly lactic acid (38.8 g/l of lactic acid and 0.4 g/l of acetic acid). The results showed that the ΔldhL1-xpk1:tkt strain had a high lactic acid yield (0.82 g per gram of consumed arabinose compared with 0.44 g per gram of consumed arabinose in the case of ΔldhL1). Moreover, the optical purity of D-lactic acid from the culture of the ΔldhL1-xpk1::tkt strain was very high at 99.9%.

Example 2

Homolactic Acid Production from Xylose

As hosts, the ΔldhL1, ΔldhL1-Δxpk1 and ΔldhL1-xpk1::tkt strains as prepared in Example 1 were used. The conditions for cultivation of *Lactobacillus plantarum* cells and PCR were the same as in Example 1. *Escherichia coli* VE 7108 (Non-Patent Document 9) and *Escherichia coli* Nova Blue (Novagen, Inc., Madison, Wis.) were used for gene manipulation of pG+host9 (Non-Patent Document 8) and pCU (Non-Patent Document 12), respectively, and grown in Luria-Bertani (LB) medium containing 250 μg/ml of erythromycin and 10 μg/ml of kanamycin and in LB medium containing 250 μg/ml of erythromycin at 37° C., respectively.

(Construction of Plasmids)

Plasmids for xylose utilization were constructed as follows. The XylAB operon (composed of from the start codon of the xylA gene to the stop codon of the xylB gene) was amplified by PCR from a genome prepared from *Lactobacillus pentosus* NRIC 1069 (obtained from NRIC) by a conventional method using oligonucleotide primers xylA_F (SEQ ID NO: 9) and xylB_R (SEQ ID NO: 10) designed based on the sequence of the xylAB operon of *Lactobacillus pentosus* MD 353 (Non-Patent Document 13). The amplified fragment was then digested with EcoRV and XhoI and subsequently inserted between the EcoRV and XhoI sites of an expression vector pCU (Non-Patent Document 12). The resulting plasmid for xylose utilization was designated as pCU-PXylAB.

A plasmid for disruption of a gene for phosphoketolase 2 (*Lactobacillus plantarum* xpk2) was constructed as follows. The 1000-bp upstream region from the start codon of the xpk2 gene and the 1000-bp downstream region from the stop codon of the same gene were amplified by PCR from the genome of *Lactobacillus plantarum* NCIMB 8826 using a pair of oligonucleotide primers xpk2-up_F (SEQ ID NO: 11) and xpk2-up_R (SEQ ID NO: 12) and a pair of xpk2-down_F (SEQ ID NO: 13) and xpk2-down_R (SEQ ID NO: 14), respectively. The resulting fragment was digested with BglII and ligated. Using the ligated fragment (2000 bp) as a template, the same fragment was amplified by PCR with oligonucleotide primers xpk2-up_F (SEQ ID NO: 11) and xpk2-down_R (SEQ ID NO: 14). The amplified fragment was digested with XhoI and SpeI and subsequently inserted between the XhoI and SpeI sites of a plasmid pG+host9. The resulting plasmid was designated as pGh9-Δxpk2.

Figure 4:
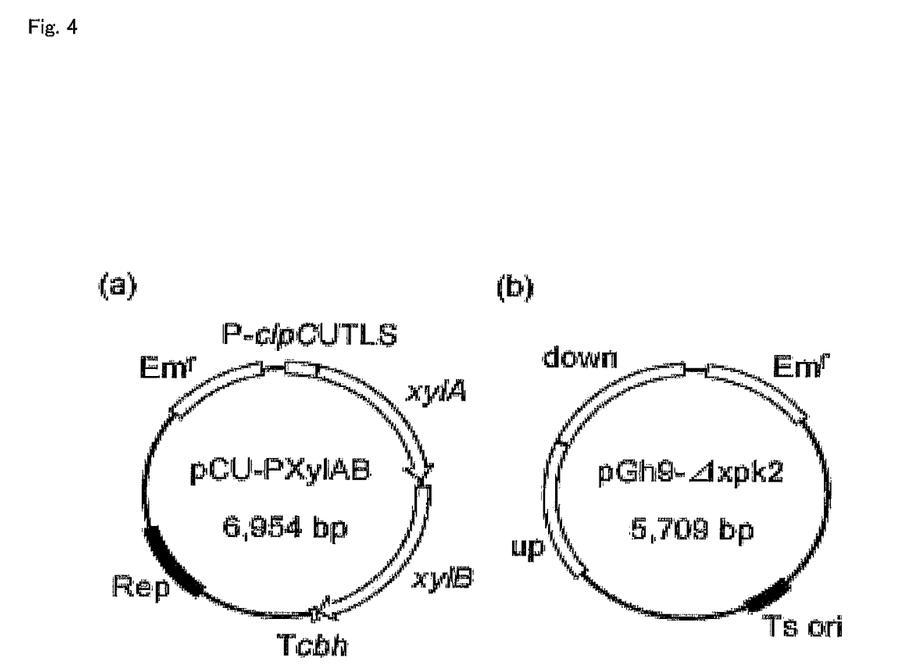
FIG. 4 is a schematic view of plasmids (a) pCU-PXylAB for xylose utilization, and (b) pGh9-Δxpk2 for disruption of a gene for phosphoketolase 2 (Lactobacillus plantarum xpk2)

FIG. 4 is a schematic view of plasmids (a) pCU-PXylAB for xylose utilization, and (b) pGh9-Axpk2 for disruption of a gene for phosphoketolase 2 (*Lactobacillus plantarum* xpk2). In (a) of FIG. 4, P-clpCUTLS represents clpCUTLS promoter; Tcbh represents terminator of cbh gene; Rep represents origin of replication; Em$^r$ represents erythromycin resistance gene; and xylA and xylB represent from the start codon of the xylA gene to the stop codon of the xylB gene. In (b) of FIG. 4, Ts Ori represents temperature-sensitive replication origin; Em$^r$ represents erythromycin resistance gene; up represents the 1000-bp upstream region from the start codon of the xpk2 gene; and down represents the 1000-bp downstream region from the stop codon of the xpk2 gene.

(Production of Xylose-Utilizing Strain)

The plasmid pCU-PXylAB was introduced into the ΔldhL1, ΔldhL1-Δxpk1 and ΔldhL1-xpk1::tkt strains by electroporation as described in Non-Patent Document 11. The resulting transformants were designated as ΔldhL1/pCU-PXylAB, ΔldhL1-Δxpk1/pCU-PXylAB, and ΔldhL1-xpk1::tkt/pCU-PXylAB, respectively.

Growth of *Lactobacillus plantarum* cells horboring pCU-PXylAB with xylose was confirmed by cultivation using xylose as the sole carbon source. A modified MRS medium (MRS without glucose, beef extract, sodium acetate, and Tween 80) containing 2.0% (w/v) xylose and erythromycin was used in this assay, and growth of *Lactobacillus plantarum* cells was monitored by measuring optical density at 600 nm ($OD_{600}$) after 15 hours of cultivation. The cells without pCU-PXylAB were also cultivated under the same conditions without erythromycin as a control.

The ΔldhL1/pCU-PXylAB strain was grown efficiently using xylose as the sole carbon source ($OD_{600}$ of 1.95). In contrast, in the case of the ΔldhL1 strain without pCU-PXylAB, growth decreased markedly ($OD_{600}$ of 0.76). This growth level is comparable to growth attained without any sugar among medium components. Also, the ΔldhL1-Δxpk1/pCU-PXylAB strain showed poor growth with xylose ($OD_{600}$ of 0.33) even compared with control cultivation ($OD_{600}$ of 0.62). This lack of growth was restored by introducing tkt into the xpk1 locus, and the ΔldhL1-xpk1::tkt/pCU-PXylAB strain showed a higher $OD_{600}$ value, 2.87, than the control cultivation ($OD_{600}$ of 0.74). These results demonstrated that an ability to utilize xylose was imparted by introducing the xylAB operon, and that the introduction of transketolase enabled xylose utilization using the PP pathway as in arabinose (Lactic Fermentation of Xylose-Utilizing Strain)

All fermentation experiments were performed in the same manner as in Example 1, except that 50 g/l of xylose was used as the sole carbon source, and erythromycin was added to the fermenter (to a final concentration of 25 g/l). The fermenter contained a xylose solution that was heat-sterilized.

Growth of *Lactobacillus plantarum* cells was monitored by measuring $OD_{600}$. The concentration of xylose and the concentrations of lactic acid and acetic acid were measured in the same manner as in Example 1. The optical purity of lactic acid was also measured and calculated in the same manner as in Example 1.

Figure 5:
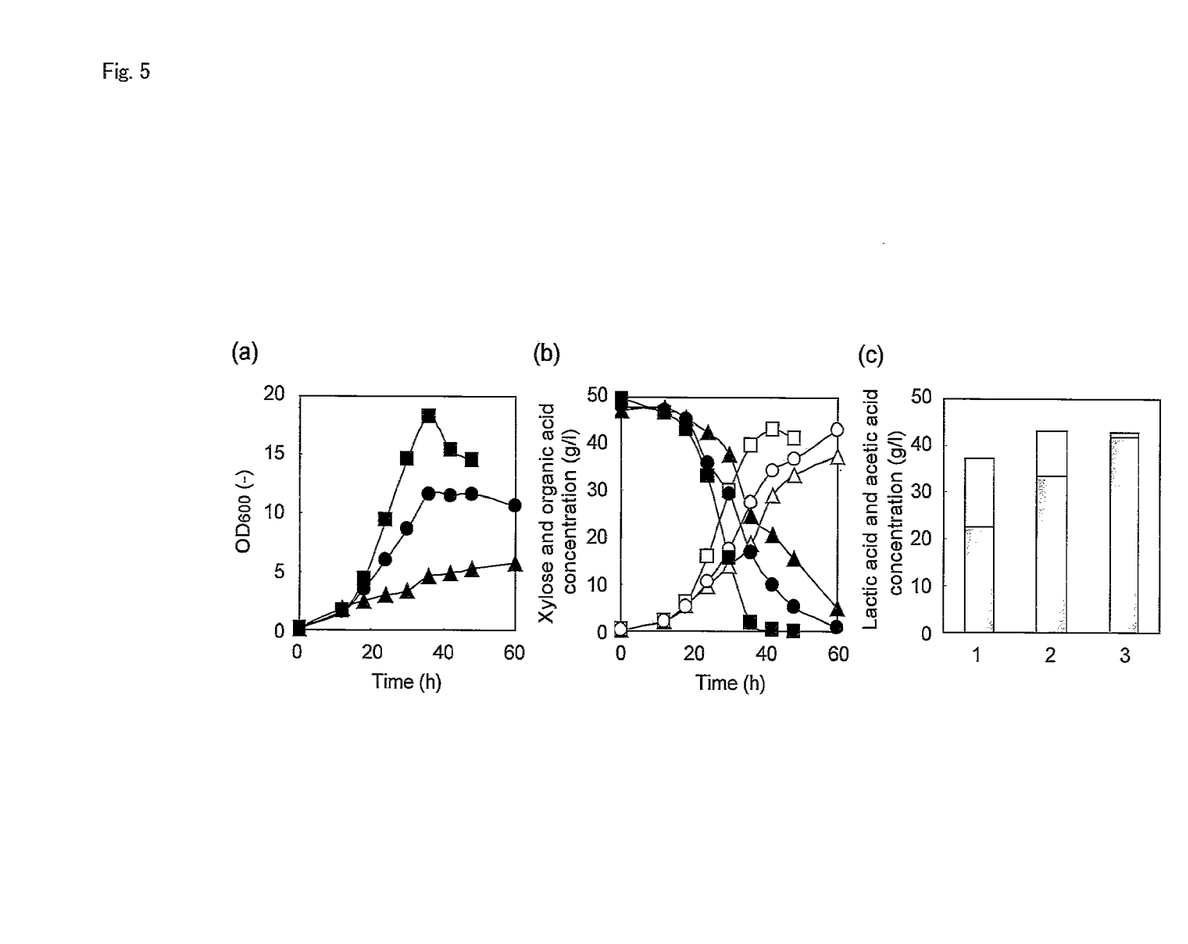
FIG. 5 shows graphs of (a) the $OD_{6000}$ of culture, (b) the concentrations of xylose and organic acid, and (c) the concentrations of lactic acid and acetic acid in fermentation experiments from xylose using the ΔldhL1/pCU-PXylAB, ΔldhL1-xpk1::tkt/pCU-PXylAB, and ΔldhL1-xpk1::tkt-Δxpk2/pCU-PXylAB strains.

FIG. 5 shows graphs of (a) the $OD_{600}$ of culture, (b) the concentrations of xylose and organic acid, and (c) the concentrations of lactic acid and acetic acid in fermentation experiments from xylose using the ΔldhL1/pCU-PXylAB and ΔldhL1-xpk1::tkt/pCU-PXylAB strains. In (a) of FIG. 5, the vertical axis represents the $OD_{600}$ value, and the horizontal axis represents the fermentation time (h). The results from the ΔldhL1/pCU-PXylAB strain are indicated by closed triangles, the results from the ΔldhL1-xpk1::tkt/pCU-PXylAB strain are indicated by closed squares. In (b) of FIG. 5, the vertical axis represents the concentrations of xylose and organic acid (both in g/l), and the horizontal axis represents the fermentation time (h). The concentration of xylose resulting from consumption by the ΔldhL1/pCU-PXylAB strain is indicated by closed triangles. The concentration of xylose resulting from consumption by the ΔldhL1-xpk1::tkt/pCU-PXylAB strain is indicated by closed squares. The organic acid (lactic acid and acetic acid combined) produced by the ΔldhL1/pCU-PXylAB strain is indicated by open triangles. The organic acid produced by the ΔldhL1-xpk1::tkt/pCU-PXylAB strain is indicated by open squares. In (c) of FIG. 5, the vertical axis represents the concentrations of produced lactic acid and acetic acid (both in gin. The concentration of lactic acid is shown below the divider in the bar, and the concentration of acetic acid is shown above the divider. The results from the ΔldhL1/pCU-PXylAB strain are shown at 1 on the horizontal axis. The results from the ΔldhL1-xpk1::tkt/pCU-PXylAB strain are shown at 2.

The ΔldhL1-xpk1::tkt/pCU-PXylAB strain showed significantly higher growth, sugar consumption, and acid production rate when compared with the ΔldhL1/pCU-PXylAB strain ((a) and (b) of FIG. 5). The $OD_{600}$ value for the ΔldhL1-xpk1::tkt/pCU-PXylAB strain increased with fermentation time and reached 18.2 after 36 hours of fermentation, while that of the ΔldhL1/pCU-PXylAB strain ($OD_{600}$ of 5.71) was much lower, even after 60 hours of fermentation ((a) of FIG. 5). Differences in sugar consumption and acid production were also observed between the strains. The ΔldhL1-xpk1::tkt/pCU-PXylAB strain consumed all sugar within 42 hours of fermentation and produced 43.2 g/l of organic acid, while fermentation continued after 60 hours with the ΔldhL1/pCU-PXylAB strain, with 37.5 g/l of organic acid being produced ((b) of FIG. 5).

As shown in (c) of FIG. 5, the ΔldhL1/pCU-PXylAB strain produced both lactic acid and acetic acid (22.6 g/l and 14.9 respectively). Unexpectedly, even when the ΔldhL1-xpk1::tkt/pCU-PXylAB strain was used, acetic acid was still produced although the production of acetic acid was partially inhibited. As a result, the ΔldhL1-xpk1::tkt/pCU-PXylAB strain produced 33.7 g/l of lactic acid and 9.6 g/l of acetic acid.

Construction of xpk2-defective strain and lactic fermentation by xylose utilization thereof.

Disruption of the xpk2 gene of the ΔldhL1-xpk1:tkt strain using pGh9-Δxpk2 was carried out by pG+host plasmid-based double-crossover homologous integration in the same manner as in Example 1. The resulting ΔldhL1-xpk1::tkt strain in which xpk2 was disrupted was designated as ΔldhL1-xpk1::tkt-Δxpk2. Deletion of xpk2 was confirmed by performing PCR using a forward primer xpk2-up_seq (SEQ ID NO: 15) and a reverse primer xpk2-down_seq (SEQ ID NO: 16) (annealed to the region from by 276 through 300 upstream of xpk2 and the region from by 268 through 300 downstream region of xpk2, respectively), comparing the bands on agarose gel electrophoresis, and DNA sequencing.

The plasmid pCU-PXylAB was introduced into the ΔldhL1-xpk1::tkt-Δxpk2 strain according to the above-mentioned method, and the resulting strain was designated as ΔldhL1-xpk1::tkt-Δxpk2/pCU-PXylAB. Lactic fermentation from xylose was examined using this strain.

FIG. 5 shows also the results of the experiment of fermentation from xylose by the ΔldhL1-xpk1::tkt-Δxpk2/pCU-PXylAB strain. In (a) of FIG. 5, the results from ΔldhL1-xpk1::tkt-Δxpk2/pCU-PXylAB strain are indicated by closed circles. In (b) of FIG. 5, the concentration of xylose resulting from consumption by the ΔldhL1-xpk1::tkt-Δxpk2/pCU-PXylAB strain is indicated by closed circles. The results for organic acid (lactic acid and acetic acid combined) produced by the ΔldhL1-xpk1::tkt-Δxpk2/pCU-PXylAB strain are indicated by open circles. In (c) of FIG. 5, the results from the ΔldhL1-xpk1::tkt-Δxpk2/pCU-PXylAB strain are shown at 3.

The disruption of xpk2 caused slight decrease of cell growth and fermentation rate ((a) and (b) of FIG. 5). However, the ΔldhL1-xpk1::tkt-Δxpk2/pCU-PXylAB strain exhibited higher fermentation performance compared to the ΔldhL1/pCU-PXylAB strain, which is a transformant of the parent ΔldhL1 strain ((a) and (b) of FIG. 5).

As shown in (c) of FIG. 5, the ΔldhL1-xpk1::tkt-Δxpk2/pCU-PXylAB strain produced predominantly lactic acid (42.0 g/l of lactic acid and 1.0 g/l of acetic acid). The results showed that the ΔldhL1-xpk1::tkt-Δxpk2/pCU-PXylAB strain provided a high lactic acid yield (0.89 g per gram of consumed xylose compared with 0.53 g per gram of consumed xylose in the case of the ΔldhL1/pCU-PXylAB strain and 0.68 g per gram of consumed xylose in the case of the ΔldhL1-xpk1::tkt/pCU-PXylAB strain). Moreover, the optical purity of D-lactic acid from the culture of the ΔldhL1-xpk1::tkt-Δxpk2/pCU-PXylAB strain was very high at 99.9%.

INDUSTRIAL APPLICABILITY

The hydrolysis product of lignocellulose pretreatment contains not only a pentose but also a hexose such as glucose, and it is desired that efficient lactic fermentation from a mixed sugar is attained in future. Furthermore, efficient lactic fermentation from not only a monosaccharide, but also an oligosaccharide or a polymer containing a series of monosaccharides is also desired. Under this circumstance, the created lactic acid bacterium of the present invention, that is capable of homolactic fermentation using a pentose as a substrate, can be useful.

The invention claimed is:

1. An isolated non-naturally occurring lactic acid bacterium capable of homolactic fermentation using a xylose as a substrate, the lactic acid bacterium utilizing a xylose, and in which a phosphoketolase pathway is blocked and a pentose phosphate pathway is activated,
wherein the lactic acid bacterium is *Lactobacillus plantarum* recombinantly produced by introducing a gene encoding a xylose isomerase and a gene encoding a xylulose kinase, causing a defect in phosphoketolase-encoding genes of xpk1 and xpk2 and introducing a gene encoding a transketolase.

2. A method for producing lactic acid, comprising: allowing the lactic acid bacterium of claim 1 to act on a xylose.

3. A method for preparing a lactic acid bacterium of *Lactobacillus plantarum* capable of homolactic fermentation using a xylose as a substrate, comprising:
causing a defect in a gene encoding a phosphoketolase in *Lactobacillus plantarum* to block a phosphoketolase pathway and introducing a gene encoding a transketolase into the *Lactobacillus plantarum* to activate a pentose phosphate pathway,
wherein the gene encoding a phosphoketolase comprises xpk1 and xpk2 and said method further comprises introducing a gene encoding a xylose isomerase and a gene encoding a xylulose kinase into the *Lactobacillus plantarum*.

4. An isolated non-naturally occurring lactic acid bacterium capable of homolactic fermentation using an arabinose as a substrate, the lactic acid bacterium utilizing an arabinose, and in which a phosphoketolase pathway is blocked and a pentose phosphate pathway is activated,
wherein the lactic acid bacterium is *Lactobacillus plantarum* recombinantly produced by causing a defect in a phosphoketolase-encoding gene of xpk1 and introducing a gene encoding a transketolase.

5. A method for producing lactic acid, comprising: allowing the lactic acid bacterium of claim 4 to act on an arabinose.

6. A method for preparing a lactic acid bacterium of *Lactobacillus plantarum* capable of homolactic fermentation using an arabinose as a substrate, comprising:
causing a defect in a gene encoding a phosphoketolase in *Lactobacillus plantarum* to block a phosphoketolase pathway and introducing a gene encoding a transketolase into the *Lactobacillus plantarum* to activate a pentose phosphate pathway,
wherein the gene encoding a phosphoketolase comprises xpk1.

* * * * *

UNITED STATES PATENT AND TRADEMARK OFFICE
CERTIFICATE OF CORRECTION

PATENT NO. : 8,715,972 B2
APPLICATION NO. : 13/202218
DATED : May 6, 2014
INVENTOR(S) : Akihiko Kondo et al.

It is certified that error appears in the above-identified patent and that said Letters Patent is hereby corrected as shown below:

In the Specification

Column 3, Line 36, after "Leuconostoc lactis" insert -- . --

Column 9, Line 21, delete "(b) pGh9-Axpk2" and insert -- (b) pGh9-Δxpk2 --

Column 9, Line 65, after "arabinose" insert -- utilization. --

Column 10, Line 35, delete "(both in gin." and insert -- (both in g/l). --

Column 11, Line 7, delete "by 276" and insert -- bp 276 --

Column 11, Line 8, delete "by 268" and insert -- bp 268 --

Signed and Sealed this
Twenty-third Day of September, 2014

Michelle K. Lee
*Deputy Director of the United States Patent and Trademark Office*

SEQUENCE LISTING

```
<160> NUMBER OF SEQ ID NOS: 16

<210> SEQ ID NO 1
<211> LENGTH: 29
<212> TYPE: DNA
<213> ORGANISM: Artificial
<220> FEATURE:
<223> OTHER INFORMATION: xpk1-up_F

<400> SEQUENCE: 1
ccgctcgagg ctgctggtca ttcggaatt                                    29

<210> SEQ ID NO 2
<211> LENGTH: 49
<212> TYPE: DNA
<213> ORGANISM: Artificial
<220> FEATURE:
<223> OTHER INFORMATION: xpk1-up_R

<400> SEQUENCE: 2
aacgagctcg tcgacagatc tttcaaaaac actccttaat ttgcttttc              49

<210> SEQ ID NO 3
<211> LENGTH: 46
<212> TYPE: DNA
<213> ORGANISM: Artificial
<220> FEATURE:
<223> OTHER INFORMATION: xpk1-down_F

<400> SEQUENCE: 3
acgcgtcgac gagctcgcag ttaaaatctt aatttgaaaa tagcgt                 46

<210> SEQ ID NO 4
<211> LENGTH: 29
```

```
<212> TYPE: DNA
<213> ORGANISM: Artificial
<220> FEATURE:
<223> OTHER INFORMATION: xpk1-down_R

<400> SEQUENCE: 4
gtggcggccg catgagcttg catggtcgg                                           29

<210> SEQ ID NO 5
<211> LENGTH: 37
<212> TYPE: DNA
<213> ORGANISM: Artificial
<220> FEATURE:
<223> OTHER INFORMATION: tkt_F

<400> SEQUENCE: 5
ggaagatcta tgtttgatac tactgatcaa ttggctg                                  37

<210> SEQ ID NO 6
<211> LENGTH: 39
<212> TYPE: DNA
<213> ORGANISM: Artificial
<220> FEATURE:
<223> OTHER INFORMATION: tkt_R

<400> SEQUENCE: 6
acgcgtcgac ttagtcaagc tctttgtatg ctttaacta                                39

<210> SEQ ID NO 7
<211> LENGTH: 19
<212> TYPE: DNA
<213> ORGANISM: Artificial
<220> FEATURE:
<223> OTHER INFORMATION: xpk1-up_seq

<400> SEQUENCE: 7
aagcactgaa ctggttgcc                                                      19

<210> SEQ ID NO 8
<211> LENGTH: 35
<212> TYPE: DNA
<213> ORGANISM: Artificial
<220> FEATURE:
<223> OTHER INFORMATION: xpk1-down_seq

<400> SEQUENCE: 8
ataattaaaa accaattaaa atatgctcac aattc                                    35

<210> SEQ ID NO 9
<211> LENGTH: 33
<212> TYPE: DNA
<213> ORGANISM: Artificial
<220> FEATURE:
<223> OTHER INFORMATION: xylA_F

<400> SEQUENCE: 9
cccgatatca tgacaaacga atattggcaa ggc                                      33

<210> SEQ ID NO 10
<211> LENGTH: 36
<212> TYPE: DNA
<213> ORGANISM: Artificial
<220> FEATURE:
<223> OTHER INFORMATION: xylB_R

<400> SEQUENCE: 10
ccgctcgagt tagtgttgtt tcctttgttc caatag                                   36
```

```
<210> SEQ ID NO 11
<211> LENGTH: 37
<212> TYPE: DNA
<213> ORGANISM: Artificial
<220> FEATURE:
<223> OTHER INFORMATION: xpk2-up_F

<400> SEQUENCE: 11
ccgctcgagt actaaaacca gatgcaaata aatgcaa                              37

<210> SEQ ID NO 12
<211> LENGTH: 47
<212> TYPE: DNA
<213> ORGANISM: Artificial
<220> FEATURE:
<223> OTHER INFORMATION: xpk2-up_R

<400> SEQUENCE: 12
ggaagatcta tatttgtttt atttatcatt acggttatta tgatagc                   47

<210> SEQ ID NO 13
<211> LENGTH: 49
<212> TYPE: DNA
<213> ORGANISM: Artificial
<220> FEATURE:
<223> OTHER INFORMATION: xpk2-down_F

<400> SEQUENCE: 13
ggaagatctg agctcagttt taatcaataa ttcagcgtaa attaaaagc                 49

<210> SEQ ID NO 14
<211> LENGTH: 30
<212> TYPE: DNA
<213> ORGANISM: Artificial
<220> FEATURE:
<223> OTHER INFORMATION: xpk2-down_R

<400> SEQUENCE: 14
ggactagtga gacgaatccc cataaaagcc                                      30

<210> SEQ ID NO 15
<211> LENGTH: 25
<212> TYPE: DNA
<213> ORGANISM: Artificial
<220> FEATURE:
<223> OTHER INFORMATION: xpk2-up_seq

<400> SEQUENCE: 15
attttggctg atcataccaa attcg                                           25

<210> SEQ ID NO 16
<211> LENGTH: 33
<212> TYPE: DNA
<213> ORGANISM: Artificial
<220> FEATURE:
<223> OTHER INFORMATION: xpk-down_seq

<400> SEQUENCE: 16
tgaaaaagaa acggaattat caactattat tta                                  33
```